United States Patent [19]

McGredy

[11] Patent Number: Plant 5,427

[45] Date of Patent: Apr. 2, 1985

[54] ROSE PLANT 'DACSHANA'

[76] Inventor: Samuel D. McGredy, 130 B Beach Rd., Castor Bay, Auckland 9, New Zealand

[21] Appl. No.: 518,092

[22] Filed: Jul. 28, 1983

[51] Int. Cl.[3] ..... A01H 5/00

[52] U.S. Cl. ..... Plt./8

[58] Field of Search ..... Plt./8

*Primary Examiner*—James R. Feyrer

*Attorney, Agent, or Firm*—Vincent G. Gioia

[57] ABSTRACT

A new miniature rose variety of near lemon yellow coloring appearing to lighten upon aging.

1 Drawing Figure

The present invention relates to a new and distinct variety of rose plant of the miniature rose class, which was originated by my crossing as seed parent the rose known as "Minueto" and the rose known as "Maybella" as pollen parent. The denomination of the new rose is "Macshana".

Among the novel characteristics possessed by this new variety which distinguish it from its parent and all other varieties of which I am aware are its lemon yellow flower coloring with small clusters of larger than average (for a miniature) blooms, upright habit of growth, quick to repeat blooming cycle suitable for pot forcing. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "13B" is plate 13B of The Royal Horticultural Society Colour Chart.

Parentage: Seedling.

*Seed parent.*—"Minueto".

*Pollen parent.*—"Maybella".

Class: Miniature (large miniatures are sometimes referred to as patio roses).

The following observations are made of specimens grown under glass in Kern County, Calif., during the month of June.

FLOWER

Blooming habit: Continuous.

Bud:

(1) *Size.*—Large.

(2) *Form.*—Ovoid.

(3) *Color.*—After sepals fall, yellow bud, near 13B, coloring lightens to near 13C.

(4) *Sepals.*—Simple, with few appendages, slightly longer than bud.

(5) *Penduncle.*—Length — short. Aspect — upright. Strength — erect. Color — near 146C.

Bloom:

(1) *Size.*—Average size when fully expanded — about 2 inches.

(2) *Borne.*—Several together in sprays.

(3) *Form.*—Ovoid opening outward to cup shaped blooms.

(4) *Petalage.*—Number of petals under normal conditions — about 20.

(5) *Color.*—Ovoid lemon yellow buds near 13B open quickly to lemon yellow flowers but with lighter tones included. Upon aging the color bleaches to paler yellow coloring. Difficult to photograph but often seen in outdoor grown plants is the tendency to have deeper yellow flower centers contrasting with paler yellow outer petals. Plants tend to bloom prolifically and the general tonality from a distance is often a mass of lemon yellow coloring.

Petals:

(1) *Texture.*—Medium.

(2) *Appearance.*—Inside velvety, outside satiny.

(3) *Form.*—Fan shaped often with pointed apices.

(4) *Arrangement.*—Imbricate.

(5) *Petaloids in center.*—Medium, 8 to 12.

(6) *Persistence.*—Drop off cleanly.

(7) *Fragrance.*—Slight.

(8) *Lasting quality.*—Very long lasting on plant and as cut flower.

REPRODUCTIVE ORGANS

Stamens, filaments and anthers:

(1) *Arrangement.*—Stamens, even length, regularly arranged around styles.

(2) *Color.*—Near 11A.

Pollen:

*Color.*—Near 17A.

Styles: Short, even, few, near 66B.

Stigmas:

*Color.*—Near 16A.

Hips: Globular, large for a miniature, near 33A, seeds do not protrude.

PLANT

Form: Upright, compact.

Growth: Vigorous, uniform.

*Height attained.*—About 18 to 24 inches.

Foliage: Compound 5 leaflets.

(1) *Size.*—Medium.

(2) *Quantity.*—Abundant.

(3) *Color.*—New foliage: Upper side — near to 144A. Under side — near to 144B. Old foliage: Upper side — near 138A. Under side — near 139C.

(4) *Shape.*—Oval, pointed.

(5) *Texture.*—Upper side is glossy and under side is glaborous.

(6) *Edge.*—Serrate.

(7) *Serration.*—Fine.

(8) *Leaf stem.*—Color — near 144B. Under side — near 144C.

(9) *Stipules.*—Long, slightly bearded.

(10) *Resistance to disease.*—Blackspot — excellent. Mildew — good. Rust — excellent.

Wood:

(1) *New wood.*—Color — near 144C. Bark — smooth.

(2) *Old wood.*—Color — near 146D. Bark — smooth.

Thorns:

(1) *Thorns.*—Quantity (main stalk) — many. On laterals from stalk — many. Form — long, pointed, slight recurve. Length — short. Color — near 144C. Position — irregular.

(2) *Prickles.*—Few to none.

Winter hardiness: Needs protection in severe climate.

I claim:

1. A new and distinct variety of rose plant of the miniature rose class, substantially as shown and described, characterized particularly by small clusters of lemon yellow flowers larger than average for miniatures, upright growing and quick repeating flower habit ideal for pot forcing.

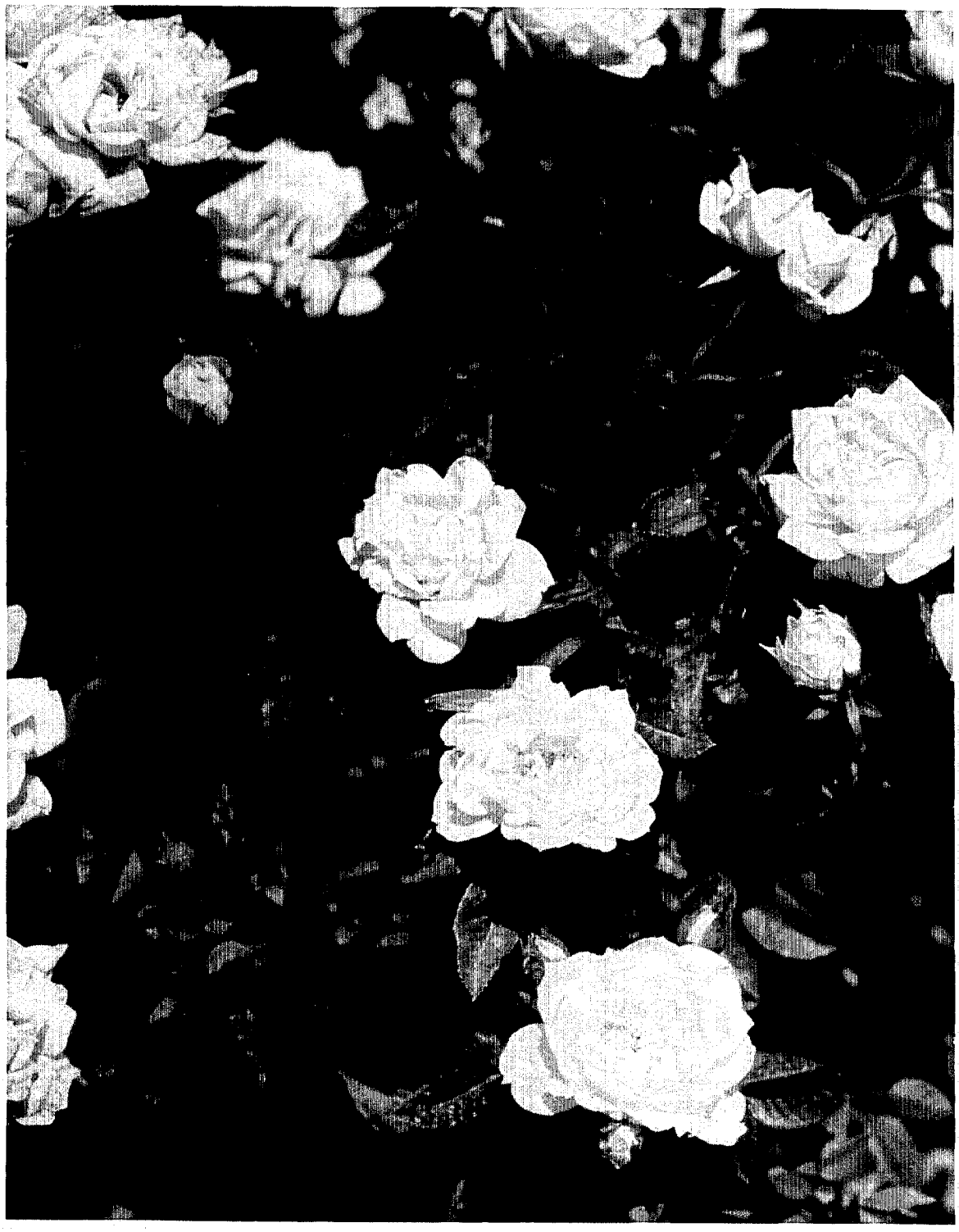

* * * * *